United States Patent [19]

Tovey et al.

[11] Patent Number: 5,674,229

[45] Date of Patent: Oct. 7, 1997

[54] SURGICAL SUTURING APPARATUS WITH LOADING MECHANISM

[75] Inventors: H. Jonathan Tovey, Milford; Corbett W. Stone, Newtown, both of Conn.; Stephen W. Zlock, Hawthorne, N.Y.; David A. Nicholas, Trumbull; Richard N. Granger, Huntington, both of Conn.; Philip Richardson, Maes-y-coed, Meidrim, St. Clears, Dyfed SA 33 5QA, Wales; Margaret Pamela Richardson, Dyfed, both of United Kingdom

[73] Assignees: United States Surgical Corporation, Norwalk, Conn.; Philip Richardson; Margaret P. Richardson, both of Wales, United Kingdom

[21] Appl. No.: 503,360

[22] Filed: Jul. 17, 1995

Related U.S. Application Data

[62] Division of Ser. No. 134,145, Oct. 8, 1993, abandoned.

[51] Int. Cl.⁶ .................................................. A61B 17/10
[52] U.S. Cl. .......................................... 606/139; 606/143
[58] Field of Search .......................... 606/139, 142–148

[56] References Cited

U.S. PATENT DOCUMENTS

| | | |
|---|---|---|
| 1,037,864 | 9/1912 | Carlson et al. . |
| 1,131,163 | 3/1915 | Saunders et al. . |
| 1,293,565 | 2/1919 | Smit . |
| 1,449,087 | 3/1923 | Bugbee . |
| 1,876,792 | 9/1932 | Thompson . |
| 2,213,830 | 9/1940 | Anastasi . |
| 2,880,728 | 4/1959 | Rights . |
| 3,090,386 | 5/1963 | Curtis . |
| 3,349,772 | 10/1967 | Rygg . |
| 3,470,875 | 10/1969 | Johnson . |
| 3,807,407 | 4/1974 | Schweizer . |
| 3,842,840 | 10/1974 | Schweizer . |
| 3,901,244 | 8/1975 | Schweizer . |
| 3,946,740 | 3/1976 | Bassett . |
| 4,021,896 | 5/1977 | Stierlein . |
| 4,109,658 | 8/1978 | Hughes . |
| 4,161,951 | 7/1979 | Scanlon, Jr. . |
| 4,164,225 | 8/1979 | Johnson et al. . |
| 4,236,470 | 12/1980 | Stenson . |
| 4,345,601 | 8/1982 | Fukuda . |
| 4,373,530 | 2/1983 | Kilejian . |
| 4,471,781 | 9/1984 | Di Giovanni et al. . |
| 4,491,135 | 1/1985 | Klein . |
| 4,580,567 | 4/1986 | Schweizer et al. . |
| 4,621,640 | 11/1986 | Mulhollan et al. . |
| 4,635,638 | 1/1987 | Weintraub et al. . |
| 4,890,615 | 1/1990 | Caspari et al. . |

(List continued on next page.)

FOREIGN PATENT DOCUMENTS

| | | |
|---|---|---|
| 0482881 | 4/1992 | European Pat. Off. . |
| 337579 | 4/1904 | France . |
| 9109097 | 9/1991 | Germany . |
| 4124383 | 5/1992 | Germany . |
| 4124381 | 8/1992 | Germany . |
| 4127812 | 2/1993 | Germany . |
| 4139628 | 3/1993 | Germany . |
| 1103854 | 8/1984 | U.S.S.R. . |
| 1505514 | 9/1989 | U.S.S.R. . |
| 1249853 | 10/1971 | United Kingdom . |
| 2260704 | 9/1991 | United Kingdom . |
| 9301750 | 2/1993 | WIPO . |

OTHER PUBLICATIONS

Aesculap Catalog, p. 401 (Date: 1905).

*Primary Examiner*—Michael Buiz
*Assistant Examiner*—Kevin Truong

[57] ABSTRACT

The invention contemplates a surgical apparatus for manipulating a surgical incision member and an associated loading mechanism for replacing the surgical incision member. The surgical apparatus comprises an elongated body portion, first and second jaw elements extending from the body portion, securing a needle for securing the surgical incision member, releasing jaw cooperating with the securing a needle for releasing the surgical incision member and locking jaw cooperating with the securing a needle for preventing at least one of the jaw elements from moving.

30 Claims, 9 Drawing Sheets

U.S. PATENT DOCUMENTS

| | | |
|---|---|---|
| 4,923,461 | 5/1990 | Caspari et al. . |
| 4,935,027 | 6/1990 | Yoon . |
| 4,957,498 | 9/1990 | Caspari et al. . |
| 5,059,201 | 10/1991 | Asnis . |
| 5,100,421 | 3/1992 | Christoudias . |
| 5,171,257 | 12/1992 | Ferzli . |
| 5,181,919 | 1/1993 | Bergman et al. . |
| 5,207,693 | 5/1993 | Phillips . |
| 5,217,471 | 6/1993 | Burkhart . |
| 5,242,458 | 9/1993 | Bendel et al. . |
| 5,254,126 | 10/1993 | Filipi et al. . |
| 5,261,917 | 11/1993 | Hasson et al. . |
| 5,281,220 | 1/1994 | Blake, III . |
| 5,336,230 | 8/1994 | Leichtling et al. . |
| 5,454,823 | 10/1995 | Richardson et al. ............ 606/148 |

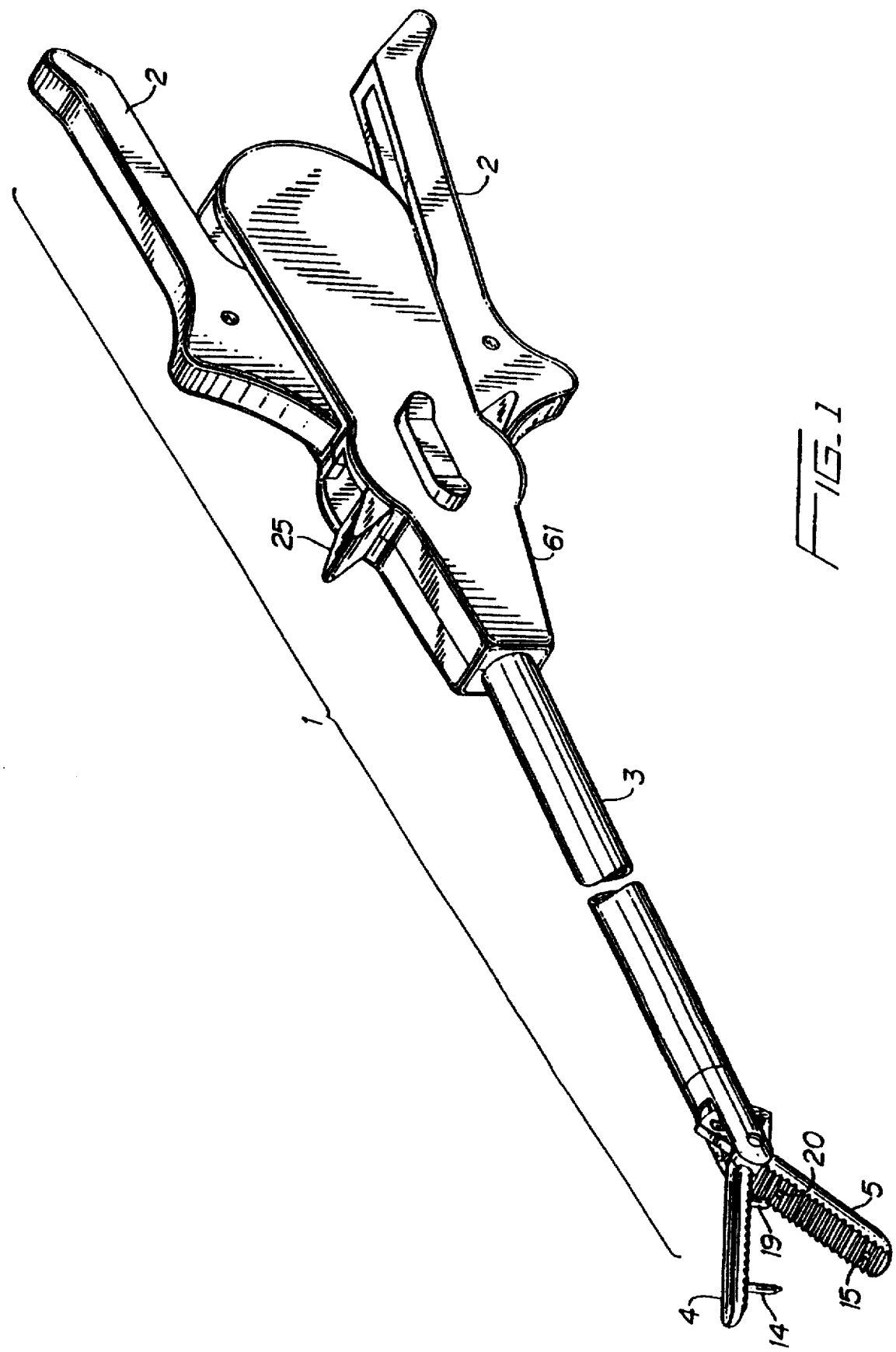

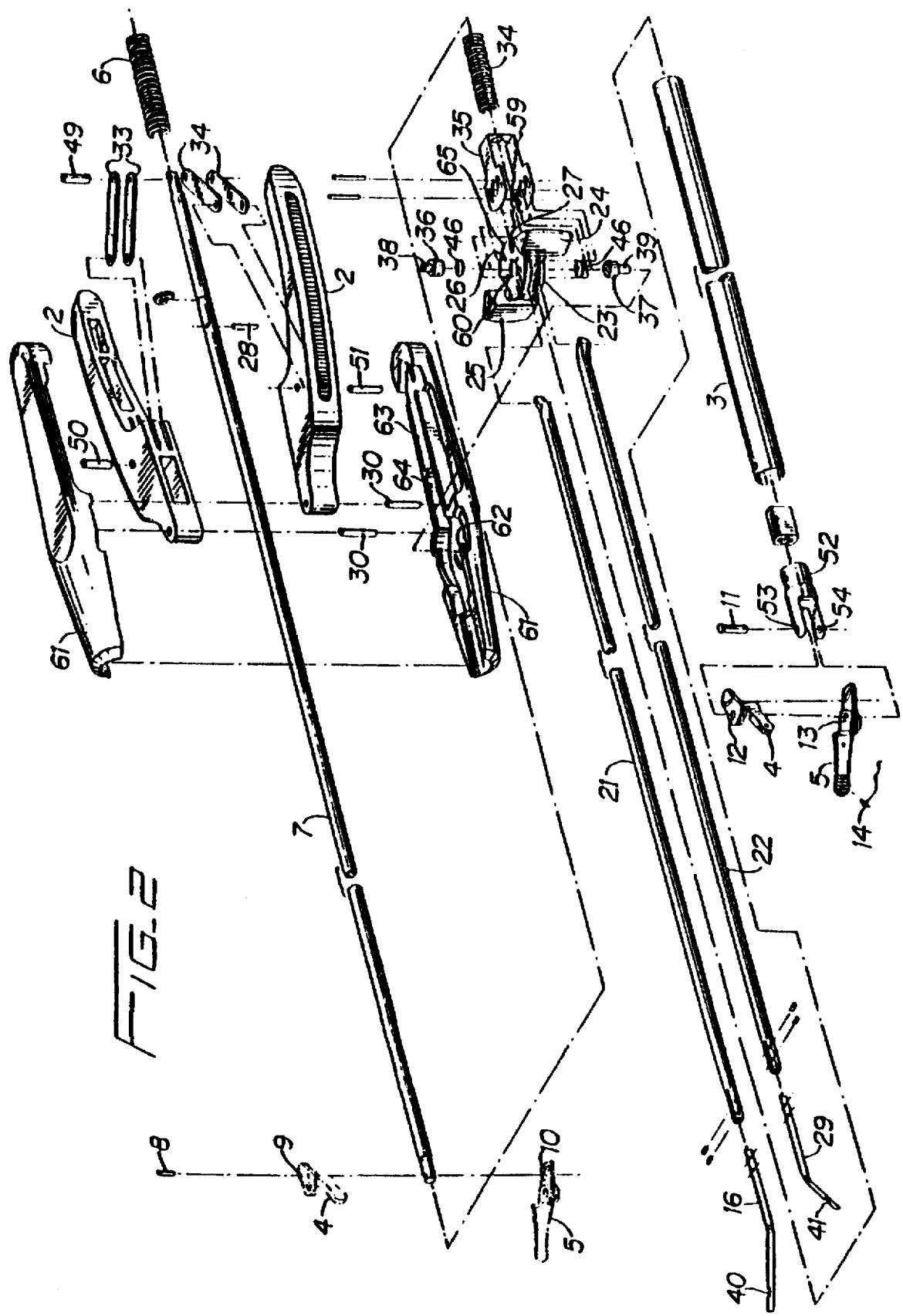

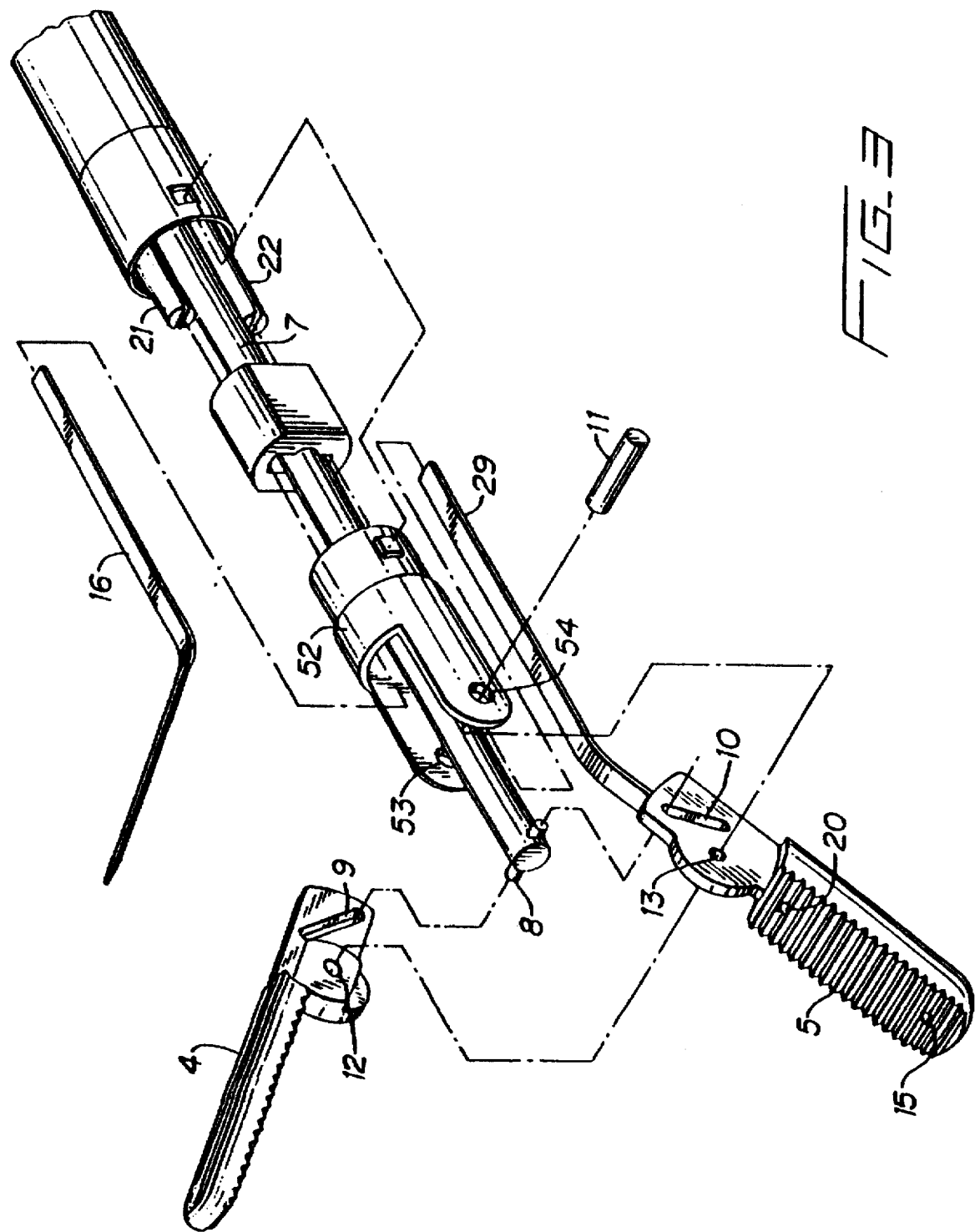

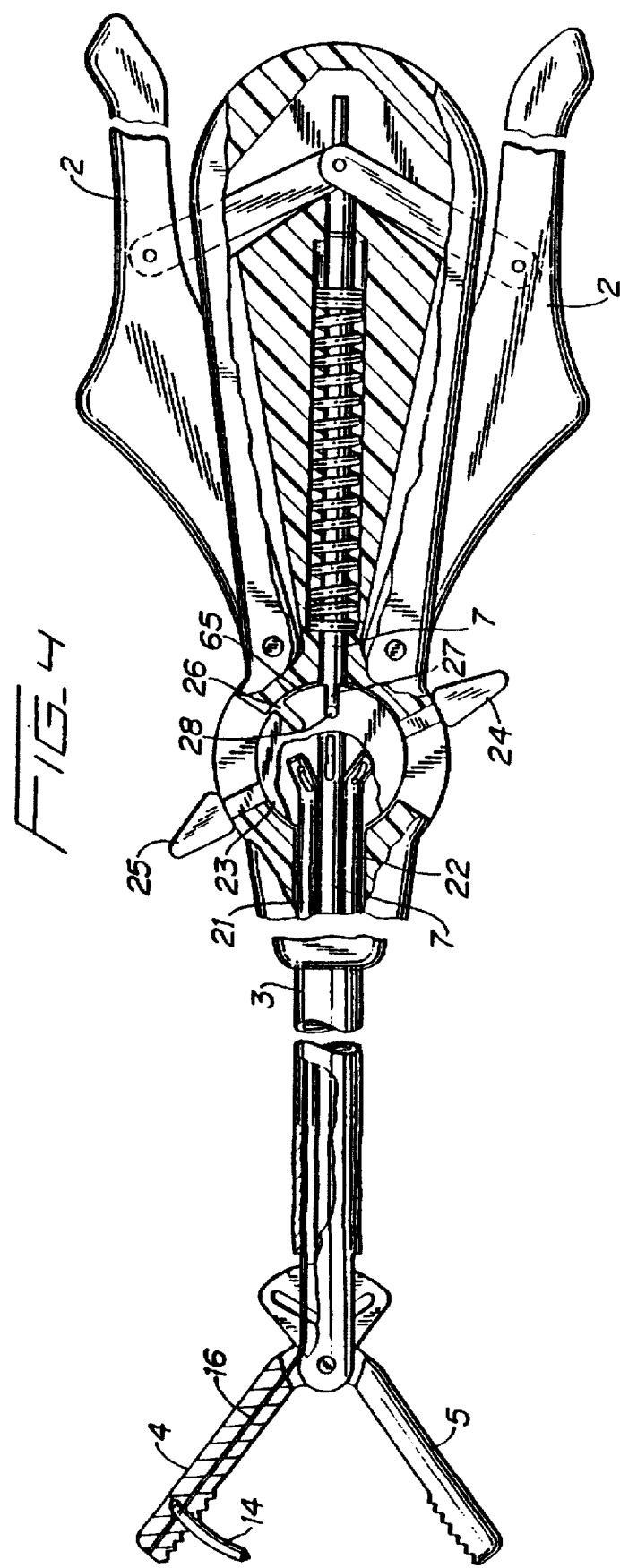

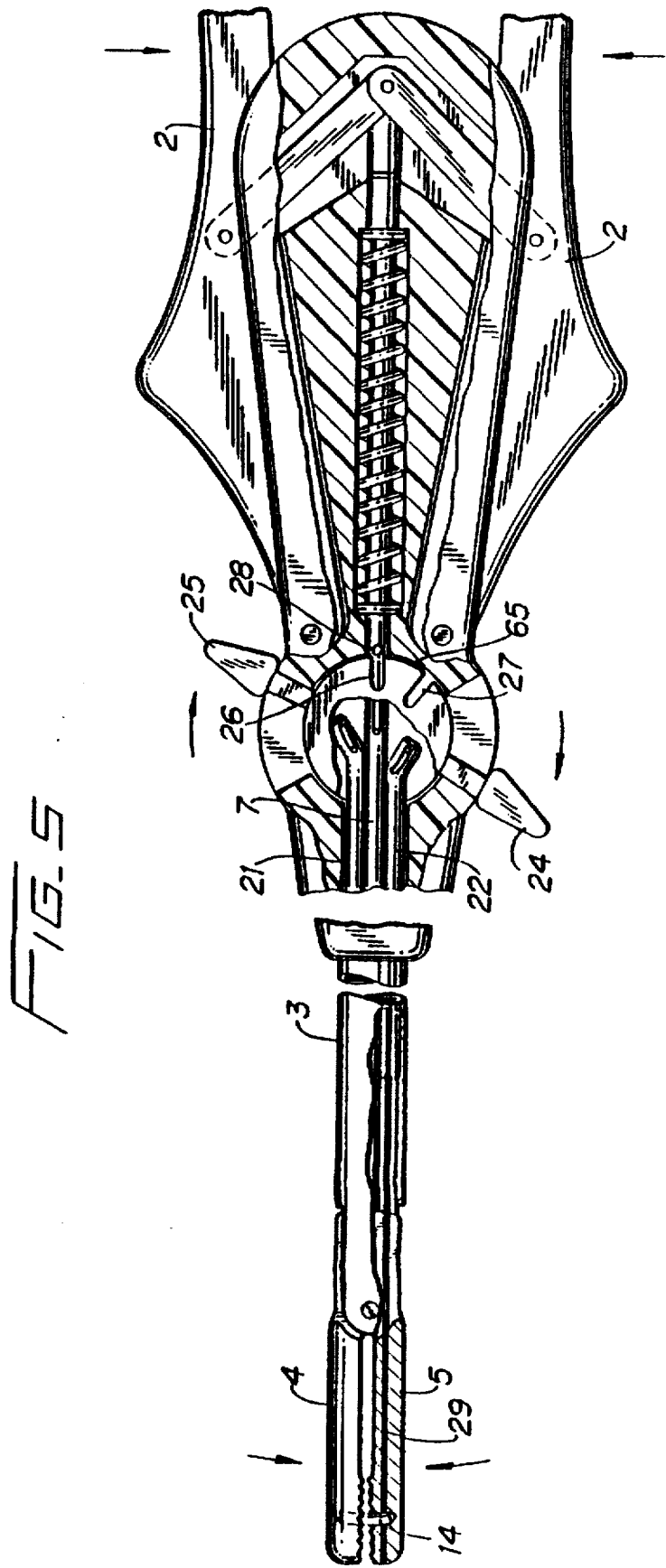

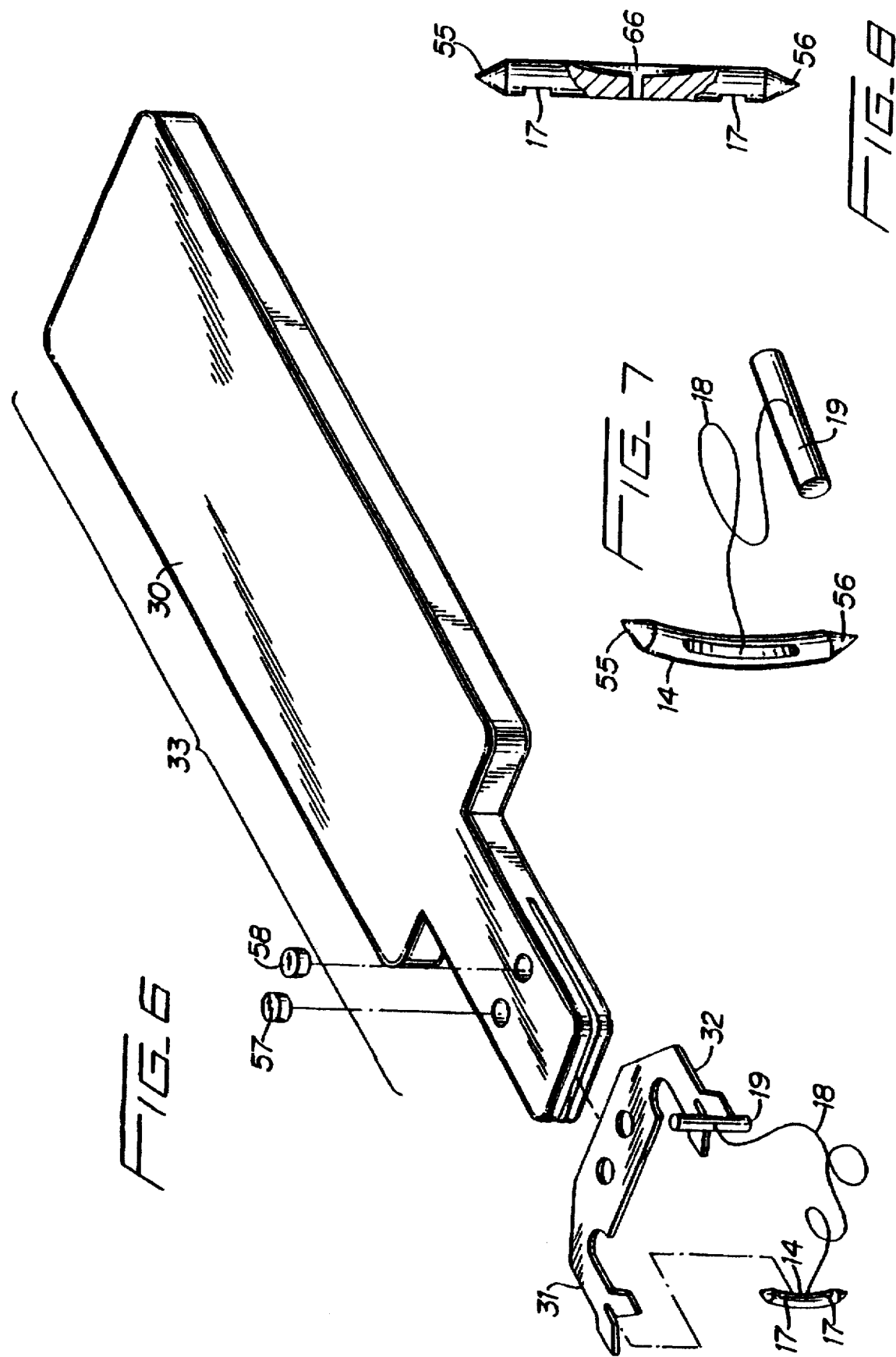

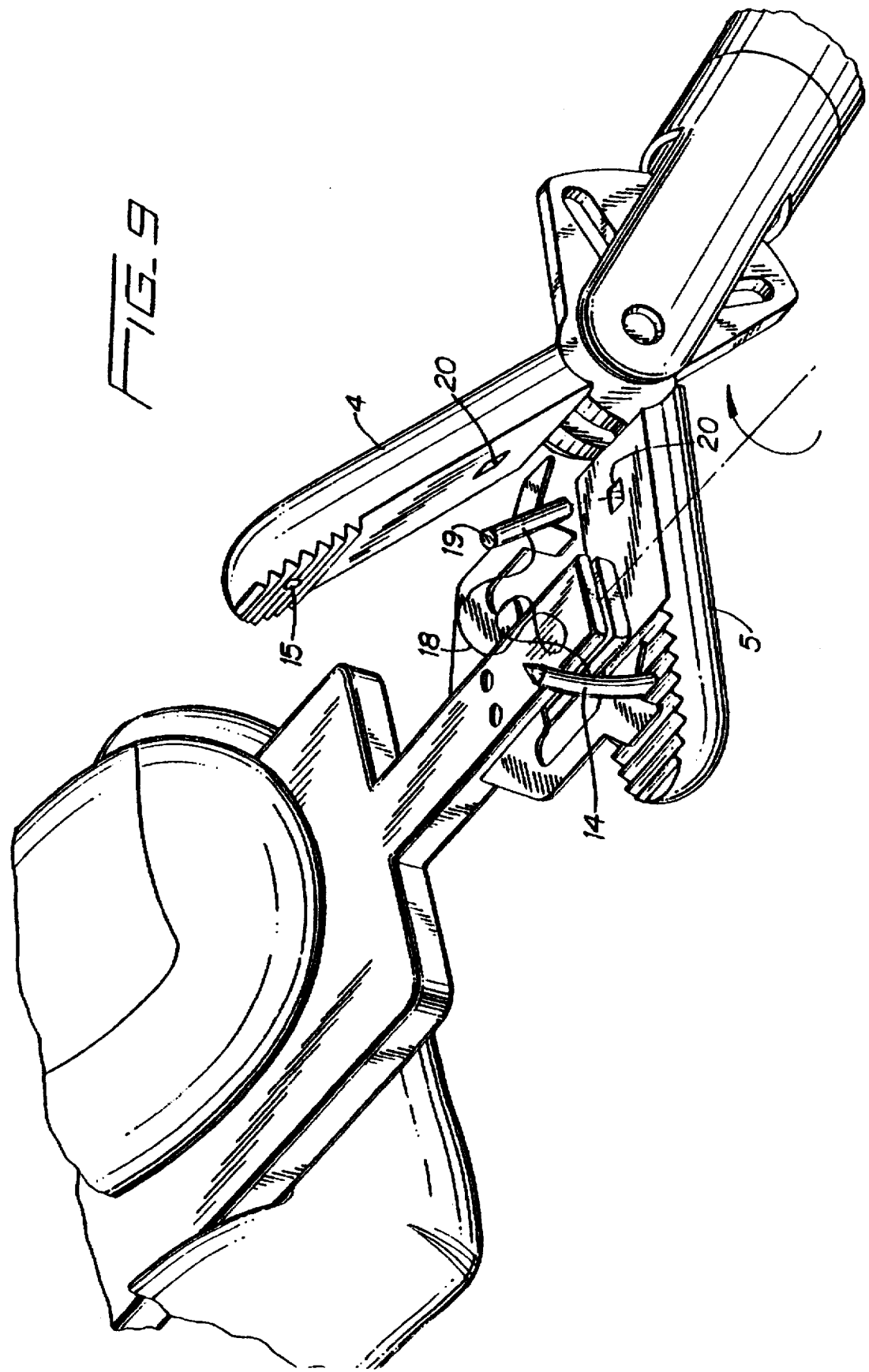

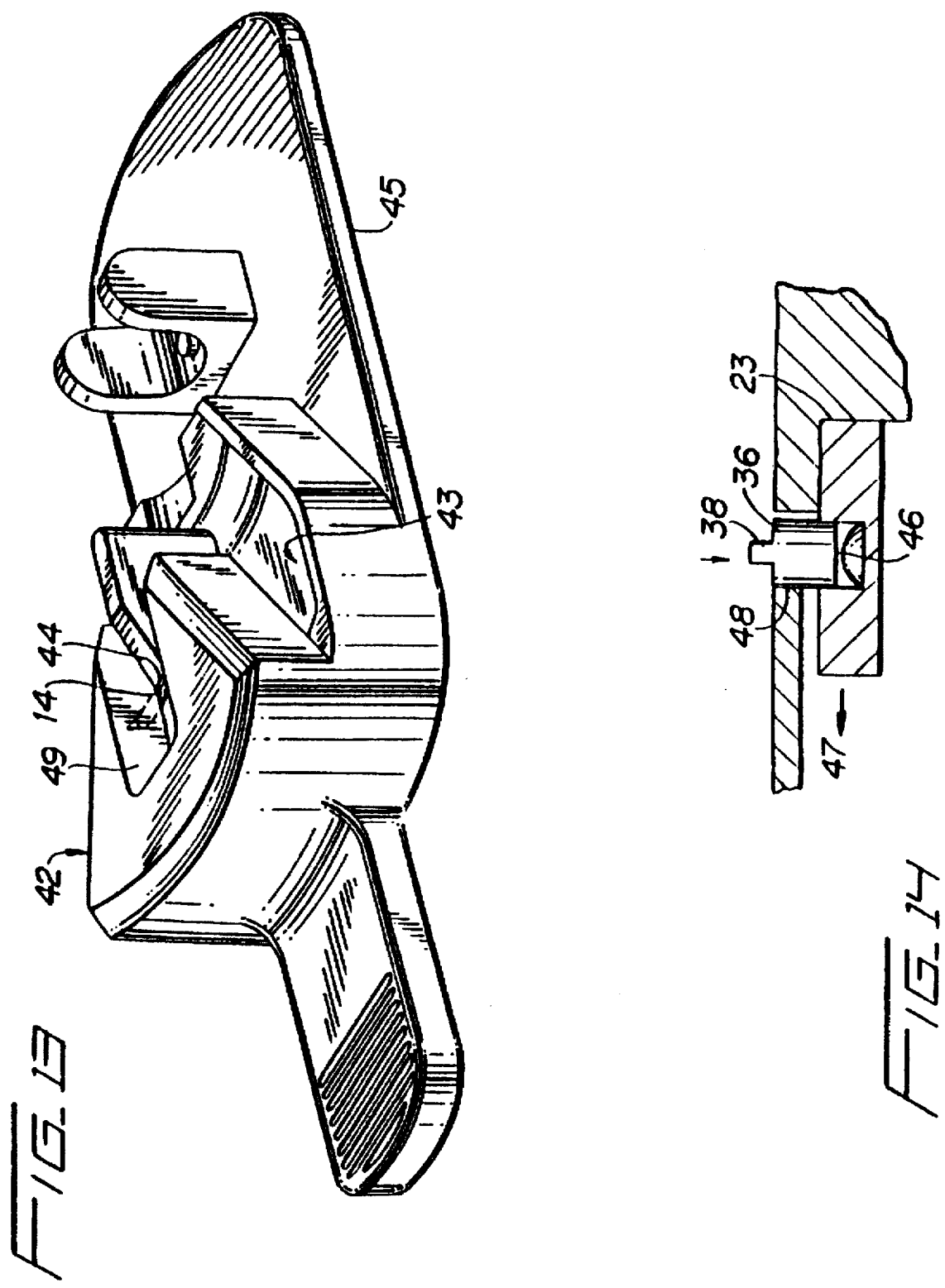

SURGICAL SUTURING APPARATUS WITH LOADING MECHANISM

RELATED APPLICATIONS

This application is a divisional of U.S. application Ser. No. 08/134,145 filed Oct. 8, 1993 now abandoned.

BACKGROUND OF THE INVENTION

1. Field of the Invention

This invention relates generally to surgical instrumentation and, more particularly, to a suturing apparatus adapted for use in endoscopic or laparoscopic surgical procedures.

2. Description of the Related Art

Endoscopic or laparoscopic procedures are characterized by the use of an elongated cannula structure having a relatively small diameter with a proximal and distal end. The distal end is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while the other cannulas may provide conduits for control of specialized surgical instruments designed for performing specific procedural functions.

Many surgical procedures call for placing stitches through tissue, a procedure traditionally accomplished by hand. Laparoscopic suturing presents a particularly challenging task, because it must be accomplished through a port that typically averages between five and ten millimeters. One instrument for facilitating laparoscopic suturing is discussed in British Patent Application no. 2260704, published Apr. 28, 1993.

Although the suturing device described in application serial no. 2260704 can be used to place laparoscopic sutures, once the suture is used up, or if a new needle is required, the suturing device must be manually re-loaded, which can be very time-consuming. As it is generally considered desirable to place 2 or 3 lines of stitching when performing an anastomosis to provide reinforcement, the laparoscopic suturing device as described in the British application mentioned above requires manual reloading one or more times. It would be advantageous to provide a laparoscopic suturing instrument to permit quick and efficient reloading of a new needle and suture. A laparoscopic suturing device would also provide an advantage if the jaws could be prevented from moving when the needle is not secured in either jaw, so as to prevent the needle from accidentally dislodging in the body cavity.

SUMMARY OF THE INVENTION

Accordingly, it is an object of the present invention to provide a surgical suturing apparatus which overcomes the drawbacks associated with prior art suturing devices.

Another object of the present invention is to provide a surgical suturing apparatus adapted for use in endoscopic and laparoscopic procedures.

A further object of the present invention is to provide a surgical suturing apparatus which is deployable within the body cavity to perform suturing therein.

Briefly stated, the invention resides in the provision of a surgical apparatus with an elongated body portion, two jaw elements extending from the body portion, securing means for securing a needle (or similar surgical incision member), the securing means cooperating with a first recess in each jaw element and releasing means cooperating with the securing means for releasing the needle secured by the securing means. In addition, locking means cooperating with said securing means for preventing the jaw elements from opening are provided to help prevent the needle from accidentally falling from the jaws. The apparatus also has an override mechanism to defeat the locking means, which makes it possible to load a new needle and suture into the device. A loading mechanism is also contemplated for this apparatus to further facilitate replacing the needle and suture.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of a surgical suturing apparatus in accordance with one embodiment of the present invention.

FIG. 2 is an exploded view of the instrument depicted in FIG. 1.

FIG. 3 is an exploded view of the jaw actuating mechanism of the instrument depicted in FIG. 1.

FIG. 4 is a plan view showing the instrument depicted in FIG. 1 with the jaws open and the needle secured in the upper jaw.

FIG. 5 is a plan view showing the instrument depicted in FIG. 1 with the jaws closed.

FIG. 6 is a perspective view of an embodiment of a loading mechanism for the apparatus of the present invention.

FIG. 7 is a perspective view of the needle, surgical thread and anchor used with the apparatus of the present invention.

FIG. 8 is a plan view of the needle used with the apparatus of the present invention.

FIG. 9 shows the loading mechanism of FIG. 6 being placed into the jaw of the apparatus.

FIG. 13 is a perspective view of an alternate embodiment of the loading mechanism used with the apparatus of the present invention.

FIG. 14 is a side view of part of the mechanism that overrides the lockout mechanism of the instrument depicted in FIG. 1.

DESCRIPTION OF THE PREFERRED EMBODIMENTS

Figure 10:
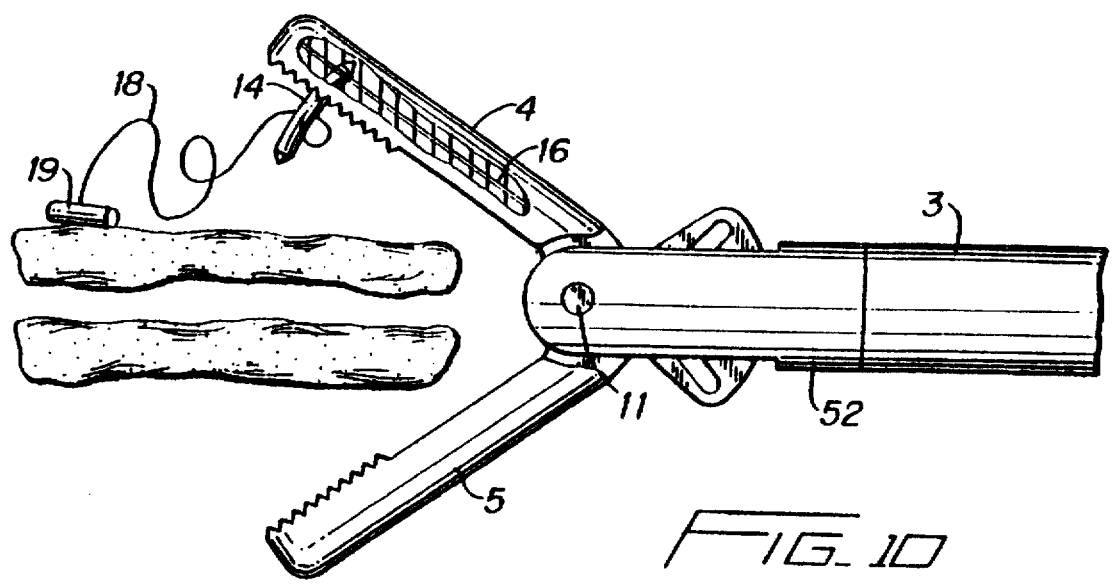
FIGS. 10, 11 and 12 show a plan view of the jaws of the instant invention as they draw the needle and connected length of suture through tissue.

Referring now to the drawings and in particular to FIG. 1, there is shown a suturing apparatus in accordance with one embodiment of the present invention. The suturing apparatus, generally indicated by reference numeral 1, has a handle housing 61 with a two-armed handle 2, an elongated tubular housing or body portion 3, and two jaws (or jaw elements) 4 and 5. Handle 2 is used to control the opening and closing of jaws 4 and 5 and may be designed to move in the same plane as jaws 4 and 5 to provide an ergonomic advantage. Handle 2 may also be rotatably connected to body portion 3 to provide further ergonomic advantage. This embodiment is particularly well adapted for use in endoscopic or laparoscopic procedures as the tubular housing 3 is preferably dimensioned to be deployable through a tubular cannula structure, e.g., of 5 mm or 10 mm internal diameter.

Referring to FIG. 2, handles 2 are connected to rod 7 by a pair of links 33 and 34 and pins 49, 50 and 51. Center rod 7 is spring biased distally by spring 6. Spring 6 fits around center rod 7 and rests in channel 63 of housing 61. When the handles 2 are squeezed, center rod 7 moves backward (proximally), causing spring 6 to be compressed. Referring to FIG. 3, the distal end of center rod 7 has a pin 8 which rides in a cam slot 9 and 10 in each of the jaws 4 and 5. Jaws 4 and 5 are pivotally connected to each other by pin 11 extending through holes 12 and 13 and through holes 53 and 54 of support 52. When center rod 7 is pulled back, pin 8 is also pulled back in cam slots 9 and 10, camming jaws 4 and 5 closed.

Referring to FIG. 3, each jaw is adapted to receive needle 14 (FIG. 7) in recess 15. When jaws 4 and 5 are closed as shown in FIG. 5, the needle 14 sits in the recess 15 in both jaws. When the jaws are opened, the needle 14 is retained in one or the other recess 15 depending on which blade 16 or 29 intersects the needle 14 through recess 17 (see FIG. 8). As shown in FIG. 4, blade 16, for example, cooperating with upper jaw element 4 has been extended into recess 17 to secure needle 14. Alternatively, blade 29 may intersect needle 14 through recess 17, securing needle 14 in jaw 5. The movement of blades 16 and 29 to engage needle 14 will be described in more detail below.

On either side of the center rod 7, side rods 21 and 22 sit inside tubular housing 3 and are connected at their proximal ends to a wheel 23 movably housed inside handle housing 61. The two halves of housing 61 are secured by pins 30. Wheel 23 has two arms 24 and 25 projecting from either side that allow the operator of the apparatus to turn wheel 23. To transfer needle 14 from jaw 4 to jaw 5, the jaws are closed and wheel 23 is rotated by turning side arm 25 clockwise so that side rod 21 is pulled back and side rod 22 is pushed forward. The side rods 21 and 22 are connected to blades 16 and 29, respectively. Therefore, when side rod 22 is pushed forward, blade 29 is pushed forward and engages needle 14 by extending into recess 17 to secure needle 14 in jaw 5. While blade 29 is in a forward position, blade 16 is in a retracted position, thus blade 16 does not contact needle 14, thereby allowing release of the needle from jaw 4. Similarly, side arm 24 may be turned counterclockwise, sliding side rod 21 and blade 16 forward and side arm 22 and blade 29 backward, thereby securing needle 14 in jaw 4 and allowing release from jaw 5. Blades 16 and 29 have notches 40 and 41, respectively, in their distal ends. These notches remain behind (proximal to) recesses 15 in jaws 4 and 5 unless the override mechanism, discussed below, is activated. When the override mechanism is activated, notches 40 and 41 align with recesses 15.

Turning now to the lockout mechanism which prevents jaws 4 and 5 from opening unless blade 16 or 29 has moved into position to secure needle 14, as shown in FIG. 2, a pin 28 extends through rod 7 which is housed proximally in wheel 23. Wheel 23 has notches 26 and 27 and abutment surface 65 therebetween. When wheel 23 is positioned so that pin 28 is aligned with the mouth of one of the notches 26, 27, the jaws 4, 5 can be opened because pin 28 has room to move forward into that notch; when wheel 23 is positioned so that pin 28 rests against abutment surface 65, jaws 4 and 5 cannot be opened because pin 28 is stopped by abutment surface 65, i.e., it does not have room to move forward.

In the initial position shown in FIG. 4, the handles 2 are open, as are jaws 4 and 5. Needle 14 is retained in jaw 4 by blade 16. In this position, pin 28 is forward in notch 27. To close jaws 4, 5 and suture body tissue, handles 2 are squeezed together, causing rod 7 and associated pin 28 to move rearwardly so that pin 28 is at the mouth of notch 27. Wheel 23 is then rotated using arms 24 or 25 to pass the needle 14 from jaw 4 to jaw 5 as described above. The rotation of wheel 23 slides pin 28 along abutment surface 65 to the mouth of notch 26. The handles can then be released, causing pin 28 to move forward into notch 26 under the force of spring 6 (discussed above), consequently moving rod 7 forward to open the jaws.

Therefore, when wheel 23 is positioned so that pin 28 is aligned with notch 26, it causes side rod 22 to be pushed into a forward position, placing blade 29 in a forward position so as to intersect needle 14 through recess 17, thereby securing needle 14 in jaw 5. When wheel 23 is positioned so that pin 28 is aligned with notch 27, it causes side arm 21 to be pushed into a forward position, placing blade 16 in a forward position so that it intersects needle 14 though recess 17, thereby securing needle 14 in jaw 4.

If the user attempts to release the handles 2 when the pin 28 is not aligned with the mouth of either notch, i.e., when wheel 23 is in position so that pin 28 is resting against (aligned with) abutment surface 65, pin 28 cannot slide forward and consequently rod 7 cannot slide forward to open the jaws 4 and 5. Thus, the locking mechanism of the present invention prevents jaws 4 and 5 from opening if needle 14 is not secured in one of the jaws by the respective blade.

Needle 14 as shown in FIG. 7 is curved, has two pointed ends 55 and 56 and is connected to a portion of surgical suture 18 in the center of needle 14. Channel 66 holds an end of the suture. To retain the suture in the needle, the suture may either be glued into channel 66 or the needle itself may be crimped. A straight needle as shown in FIG. 8 may also be utilized, and the suture can be connected adjacent one of the ends (not shown). A single-pointed needle could also be alternatively provided (not shown). The opposite end of suture 18 may also have an anchor 19 affixed thereto for securing the suture in tissue.

Figure 11:
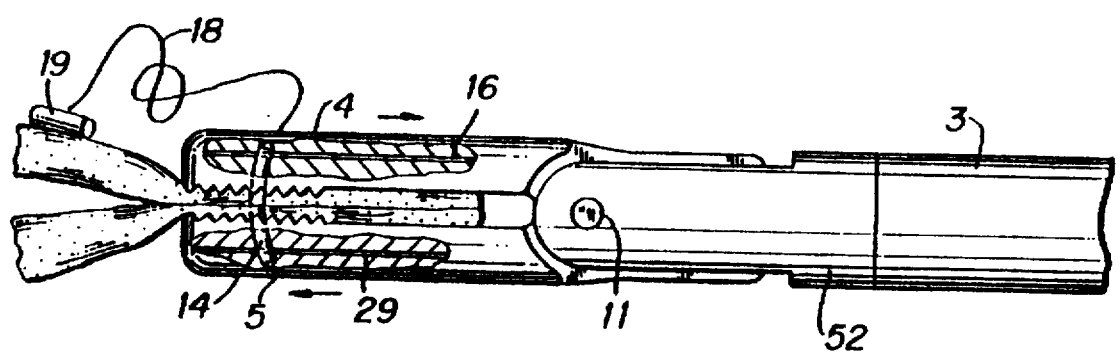
Figure 12:
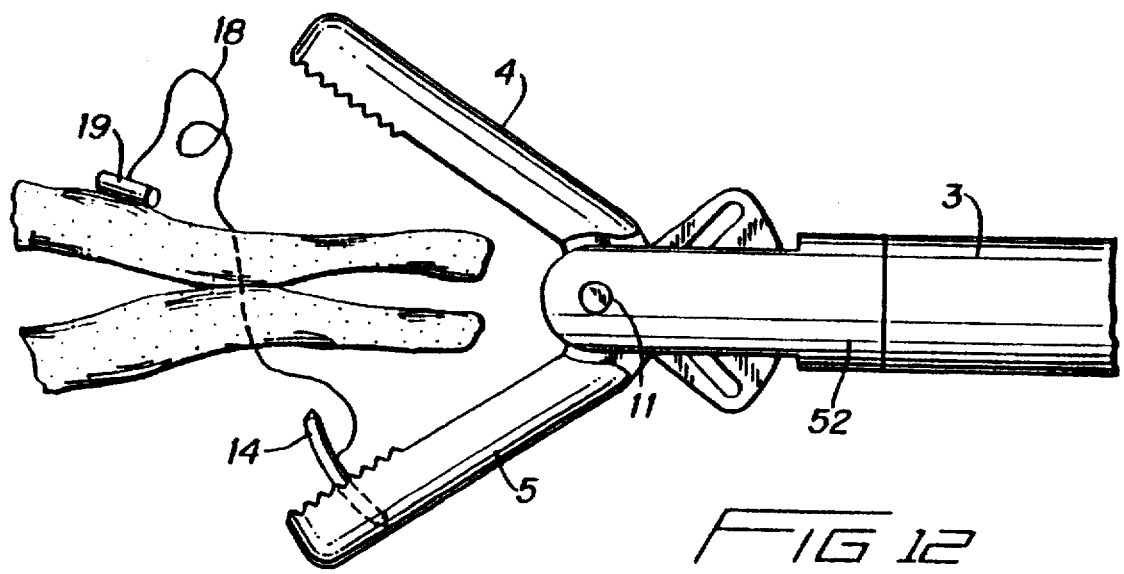

Referring to FIGS. 10, 11 and 12, to operate the suturing apparatus of the instant invention, the open jaws 4, 5 are positioned around the tissue to be sutured. Note that needle 14 is shown held securely in jaw 4 by blade 16. Handles 2 are squeezed, closing the jaws 4, 5 around the tissue and piercing it with needle 14, which is held securely in jaw 4 by blade 16. As needle 14 pierces the tissue, it is guided into a recess 15 in the opposite jaw 5. If the jaws are open, pin 28 is positioned forward in notch 26 or 27 as described above, and consequently wheel 23 cannot move until the jaws are closed and pin 28 can then travel along abutment surface 65. With the jaws closed, wheel 23 may be moved by turning side arm 25 clockwise, thereby sliding blade 16 out of one end of the needle 14 and simultaneously sliding blade 29 into the other end of the needle. This clockwise movement slides pin 28 from the mouth of notch 27 to the mouth of notch 26 as described above. Thus, by turning side arm 25 (and wheel 23), needle 14 is released from jaw 4 and engaged in jaw 5. The needle 14 will then be positioned in the jaw 5, drawing suture 18 through the tissue. Anchor 19 will rest on the tissue, thereby securing suture 18 in the tissue. The jaws 4 and 5 are then opened by releasing the handles. If the needle 14 is double-pointed, the instrument is ready to make another stitch. To do so, the handles 2 are squeezed and the jaws are again closed. After closing the jaws to make the second stitch, the needle 14 can be passed back to jaw 4 by rotating side arm 24 of wheel 23 to slide blade 16 distally and blade 29 proximally. If the needle has only one point, the needle must be transferred back to the opposite jaw (by closing the jaws and rotating wheel 23) before the instrument is ready to make another stitch.

In order to load the suturing apparatus, jaws 4 and 5 must be opened and still allow needle 14 to be removed and a replacement needle to be loaded into slot 15. This cannot be accomplished if either blade 16 or 29 is intersecting slot 15 in accordance with the securing mechanism described above. Therefore, a mechanism to override the lockout mechanism described above is provided, as shown in FIGS. 2 and 14. U-channel 35 straddles wheel 23. Spring 34 is seated within channel 64 of housing 61 and is proximal to U-channel 35 and wheel 23. Rod 7 extends through spring 34, hole 59 in U-channel 35 and wheel 23. Plungers 36 and 37 each rest in hole 60 on either side of wheel 23 and each plunger extends through U-channel 35. Each plunger 36, 37, rests upon a spring washer 46, which also rests in hole 60 in wheel 23. Plungers 36 and 37 have a smaller-diameter knobs 38 and 39, respectively, extending therefrom and through housing 61.

As shown in FIGS. 2 and 14, housings 61 have channels 62 in which knobs 38 and 39, respectively, may move back and forth freely. Plungers 36 and 37, however, rest against surface 48 in housing 61. When knobs 38 and 39 are pushed down, spring washers 46 compress, plungers 36 and 37 clear surfaces 48 and ride forward (distally) into recesses 47, propelled by the energy of compressed spring 34.

Therefore, to operate this override mechanism, side arms 24 and 25 are positioned so that pin 28 is abutting abutment surface 65 and cannot ride forward into notches 26 or 27. Knobs 38 and 39 are pushed down, thereby causing wheel 23 to ride forward into recesses 47 of housing 61. As wheel 23 rides forward, so do pin 28 and rod 7, thereby allowing jaws 4 and 5 to open.

When wheel 23 is propelled forward as described above, side rods 21 and 22 and blades 16 and 29 are driven forward sufficiently so that notches 40 and 41 align with recess 15 in each jaw. When notches 40 and 41 align with recess 15, blades 16 and 29 are technically in a forward position (which allows the jaws to be opened because the lockout mechanism described above is only actuated if neither blade is in a forward position). In this position, however, recesses 15, instead of being intersected by blades 16 and 29, are aligned with notches 40 and 41 so that recesses 15 are clear all the way through in each jaw, thereby allowing the old needle 14 to be removed from the instrument and a new needle 14 to be replaced. Thus, the lockout mechanism discussed above has been defeated by the override mechanism, because the jaws 4, 5 are open, and yet the needle 14 is not secured. After the new needle has been inserted, side arms 24 and 25 can be pulled proximally, compressing spring 34 and re-engaging lower knobs 36 and 37 with surface 48, thereby re-arming the lockout mechanism of this instrument.

Referring to the loading mechanism for replacing the needle, suture and anchor of the present invention shown in FIG. 13, needle 14 is positioned in notch 44 and recesses 42 and 43 of the loading mechanism are configured to receive jaws 4 and 5. When jaws 4 and 5 are closed, the needle 14 becomes engaged in jaw 4 and the closed jaws are removed from the loading mechanism by lifting them through recess 49. The body portion of this loading mechanism 45 may be hollow, thereby holding a package containing suture and anchor inside it.

FIG. 6 shows another embodiment of a loading mechanism 33 for replacing the needle, suture and anchor of the present invention. The loading mechanism consists of handle 30 and arms 31 and 32 attached thereto via fasteners 57 and 58. Each arm is adapted to hold either an anchor/positioning element 19 or a needle 14. The anchor/positioning element 19 and the needle 14 are preferably approximately the same diameter so that both arms 31 and 32 may be of similar dimension.

Referring to FIG. 9, each jaw may be adapted to hold anchor 19 shown in FIG. 6. Recess 20 is one adaptation suitable to hold the suture anchor. The distance between the needle's recess 15 and the anchor's recess 20 approximately equals the distance between the needle 14 and anchor 19 in the loading mechanism to facilitate proper loading. Suture anchor 19 can be fixedly attached to needle 14 by suture 18. Suture anchor 19 may also help guide and position needle 14 into recess 15. If anchor 19 is not properly placed in recess 20, jaws 4 and 5 cannot close. If anchor 19 is properly placed, however, this placement helps guide the position of needle 14 into recess 15. Alternatively, a separate positioning element may be provided. In yet another embodiment, positioning element 19 is fixedly attached to loading mechanism 33 and is placed into recess 20 for positioning purposes, but is drawn away when the loading mechanism 33 is removed from the suturing apparatus.

To reload a needle, anchor and suture into the apparatus, the override mechanism described above would be activated and the old needle removed. As shown in FIG. 9, to reload the apparatus utilizing loading mechanism 33, mechanism 33 is held perpendicular to the bottom open jaw 5 and the needle 14 and the anchor/positioning element 19 are placed into their respective recesses (15 and 20) one at a time. After the needle 14 and anchor/positioning element 19 are placed in their respective recesses, the jaws 4, 5 are closed, and the loading mechanism 33 is pulled away, leaving the needle 14 and anchor 19 in place.

Regardless of the loading mechanism employed, once a new needle, suture and anchor are loaded into jaws 4 and 5, the lockout mechanism must then be re-armed, as described above, by pulling knobs 38 and 39 proximally so that plungers 36 and 37 re-engage surface 48 of housing 61. Wheel 23 must then be turned, placing blade 16 or 29 in a forward position so that it intersects needle 14, thereby retaining needle 14 when jaws 4 and 5 are opened, allowing the instrument to pierce another portion of tissue.

The foregoing is considered illustrative only of the principles of the invention. Further, the invention is not intended to be limited to the exact construction and operation shown and described. Accordingly, all suitable modifications and equivalents fall within the scope of this invention.

We claim:

1. Surgical apparatus for manipulating a surgical incision member comprising an elongated body portion;

first and second jaw elements extending from said body portion, at least one of said jaw elements being movable between an open and closed position, each of said jaw elements having a recess;

securing means engageable with the surgical incision member for securing a portion of the surgical incision member in one of said recesses, said securing means movable between a first position to secure the surgical incision member and a second position to release the surgical incision member; and locking means operatively connected to said securing means for preventing said securing means from releasing the surgical incision member when said jaw elements are in said open position.

2. Surgical apparatus according to claim 1, further comprising override means operatively connected to said locking means for permitting said jaw elements to open when the surgical incision member is not secured in either of said jaw elements.

3. Surgical apparatus according to claim 1, further comprising the surgical incision member, said surgical incision member having two pointed ends, both ends engageable with said securing means.

4. Surgical apparatus according to claim 1, wherein said securing means comprises a moveable blade engageable with the surgical incision member.

5. Surgical apparatus according to claim 1, further comprising first and second handles positioned at a proximal end of said body portion for moving said jaw elements, wherein said first and second handles move in the same plane as said jaw elements.

6. Surgical apparatus according to claim 5, wherein said first and second handles are rotatably attached to said body portion.

7. Surgical apparatus for manipulating a surgical incision member comprising an elongated body portion;

first and second jaw elements extending from said body portion;

a handle mechanism for moving at least one of said jaw elements between an open and closed position;

receiving means in each said jaw element for receiving a portion of the surgical incision member;

securing means engageable with the surgical incision member and movable between a first position to secure the surgical incision member in one of said jaw elements and a second position to release the surgical incision member from one of said jaw elements; and locking means operatively connected to said securing means for preventing said at least one jaw element from moving to said open position when the surgical incision member is not secured in either of said jaw elements.

8. Surgical apparatus according to claim 7, further comprising override means operatively connected to said locking means for permitting said jaw elements to open when the surgical incision member is not secured in either of said jaw elements.

9. Surgical apparatus according to claim 7, wherein said receiving means comprises a first recess in each said jaw element.

10. Surgical apparatus according to claim 7, further comprising the surgical incision member, said surgical incision member having two pointed ends, both ends engageable with said securing means.

11. Surgical apparatus according to claim 7, wherein said securing means comprises a slidable elongated member engageable with the surgical incision member.

12. Surgical apparatus according to claim 7, further comprising control means positioned at a proximal end of said body portion for moving said jaw elements, wherein said control means moves in the same plane as said jaw elements.

13. Surgical apparatus according to claim 12 wherein said control means is rotatably attached to said body portion.

14. Surgical apparatus for manipulating a surgical incision member comprising an elongated body portion defining a longitudinal axis;

first and second jaw elements extending from said body portion, at least one of said jaw elements being movable between an open and closed position, each of said jaw elements having a first recess;

a surgical incision member comprising a needle pointed at two ends, both ends supported by one of said first and second jaw elements in said first recess;

at least one elongated member engageable with said needle pointed at two ends and movable between a first position to secure said needle and a second position to release said needle; and a handle mechanism positioned at a distal end of said body portion for moving said jaw elements, said handle mechanism including two arms moveable toward the longitudinal axis defined by said elongated body portion.

15. Surgical apparatus for manipulating a surgical incision member comprising an elongated body portion defining a longitudinal axis;

first and second jaw elements extending from said body portion, at least one of said jaw elements being movable between an open and closed position, each of said jaw elements having a first recess;

a surgical incision member supported by one of said first and second jaw elements in said first recess;

at least one elongated member engageable with said surgical incision member and movable between a first position to secure said surgical incision member and a second position to release said surgical incision member; and a handle mechanism positioned at a distal end of said body portion for moving said jaw elements, said handle mechanism including two arms moveable toward the longitudinal axis defined by said elongated body portion, wherein said handle mechanism is rotatably attached to said body portion.

16. Surgical apparatus for manipulating a surgical incision member comprising an elongated body portion defining a longitudinal axis;

first and second jaw elements extending from said body portion, at least one of said jaw elements being movable between an open and closed position;

receiving means in each said jaw element for receiving a portion of the surgical incision member;

securing means movable with respect to said receiving means between a first position to secure the surgical incision member in one of said jaw elements and a second position to release the surgical incision member from one of said jaw elements;

moving means for moving said securing means; and control means positioned at a proximal end of said body portion for moving said jaw elements, said control means including two arms moveable toward the longitudinal axis defined by said elongated body portion.

17. Surgical apparatus according to claim 16, wherein said receiving means comprises a first recess in each said jaw element.

18. Surgical apparatus according to claim 16, further comprising the surgical incision member, said surgical incision member having two pointed ends, both ends engageable with said securing means.

19. Surgical apparatus according to claim 16, wherein said securing means comprises a blade engageable with the surgical incision member.

20. Surgical apparatus according to claim 16, wherein said control means is rotatably attached to said body portion.

21. Surgical apparatus for manipulating a surgical incision member comprising an elongated body portion having a proximal and distal portion;

first and second jaw elements extending from the distal portion of said body portion, at least one of said jaw elements being movable between an open and closed position;

a surgical incision member supported by one of said jaw elements; and a handle extending from the proximal portion of said body portion for moving said jaw elements; wherein said at least one jaw element is prevented from moving when said surgical incision member is not secured in at least one of said jaw elements.

22. Surgical apparatus of claim 21, further comprising an override mechanism housed within said handle to allow said at least one jaw element to move when said surgical incision member is not secured in at least one of said jaw elements.

23. Surgical apparatus according to claim 21, wherein said surgical incision member comprises a needle pointed at two ends.

24. Surgical apparatus according to claim 21, wherein said handle moves in the same plane as said jaw elements.

25. Surgical apparatus according to claim 21, wherein said handle is rotatably attached to said body portion.

26. Surgical apparatus comprising an elongated body portion having a proximal and distal portion;

first and second jaw elements extending from the distal portion of said body portion, at least one of said jaw elements being movable between an open and closed position;

a surgical incision member supported by one of said first and second jaw elements;

a securing mechanism moveable with respect to said jaw elements between a first position to secure said surgical incision member in said first jaw element and a second position to secure said surgical incision member in said second jaw element;

a mechanically actuable jaw closing mechanism operatively connected to said jaw elements for selectively controlling the movement of said jaw elements between said open and closed positions; and a mechanically actuable control mechanism operatively connected to said securing mechanism for selectively controlling movement of said securing mechanism between said first and second positions.

27. The surgical apparatus of claim 26, wherein said control mechanism is a rotatable wheel.

28. The surgical apparatus of claim 26, wherein said jaw closing mechanism has at least one handle and a reciprocating rod operatively connecting said at least one handle to at least one of said jaw elements.

29. The surgical apparatus of claim 26, wherein said at least one handle is prevented from moving when said surgical incision member is not secured in either of said jaw elements.

30. The surgical apparatus of claim 26, wherein said control mechanism is prevented from moving when said at least one jaw element is in said open position.

* * * * *